(12) United States Patent
Kueenzi et al.

(10) Patent No.: US 9,005,295 B2
(45) Date of Patent: Apr. 14, 2015

(54) LOW PROFILE INTERVERTEBRAL IMPLANT

(75) Inventors: Thomas Kueenzi, Downingtown, PA (US); Ryan Walsh, Douglassville, PA (US); Tom Pepe, Turnersville, NJ (US); Markus Hunziker, Aarau (CH); David Koch, Bubendorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/594,965

(22) Filed: Aug. 27, 2012

(65) Prior Publication Data

US 2012/0323330 A1 Dec. 20, 2012

Related U.S. Application Data

(63) Continuation of application No. 12/743,098, filed as application No. PCT/US2008/082473 on Nov. 5, 2008, now Pat. No. 8,540,774.

(60) Provisional application No. 60/988,661, filed on Nov. 16, 2007.

(51) Int. Cl.
*A61F 2/44* (2006.01)
*A61B 17/70* (2006.01)
(Continued)

(52) U.S. Cl.
CPC . *A61F 2/447* (2013.01); *A61F 2/44* (2013.01); *A61B 17/7059* (2013.01); *A61B 17/8033* (2013.01); *A61B 17/86* (2013.01); *A61F 2/28* (2013.01); *A61F 2002/30077* (2013.01); *A61F 2002/30092* (2013.01); *A61F 2002/302* (2013.01); *A61F 2002/30331* (2013.01);
(Continued)

(58) Field of Classification Search
USPC .......................................... 623/17.11–17.16
See application file for complete search history.

(56) References Cited

U.S. PATENT DOCUMENTS 1,105,105 A 7/1914 Sherman
2,621,145 A 12/1952 Sano
(Continued)

FOREIGN PATENT DOCUMENTS

CA 2317791 8/1999
DE 3042003 7/1982
(Continued)

OTHER PUBLICATIONS

Synthes SynFix-LR System Technique Guide dated 2008.
(Continued)

*Primary Examiner* — Andrew Yang
*Assistant Examiner* — Diana S Jones
(74) *Attorney, Agent, or Firm* — Baker & Hostetler, LLP

(57) ABSTRACT

The present invention is directed to a low profile intervertebral implant (10) for implantation in an intervertebral disc space (D) in-between adjacent vertebral bodies (V). The intervertebral implant includes a plate (40) preferably coupled to a spacer (20). The plate is preferably formed from a first material and the spacer is preferably formed from a second material, the first material being different from the second material. The plate is preferably sized and configured so that the plate does not extend beyond the perimeter of the spacer. In this manner, the plate preferably does not increase the height profile (hs) of the spacer and the plate may be implanted within the intervertebral disc space in conjunction with the spacer.

26 Claims, 10 Drawing Sheets

(51) Int. Cl.
- *A61B 17/80* (2006.01)
- *A61B 17/86* (2006.01)
- *A61F 2/28* (2006.01)
- *A61F 2/30* (2006.01)

(52) U.S. Cl.
CPC ............... *A61F2002/30387* (2013.01); *A61F 2002/30485* (2013.01); *A61F 2002/305* (2013.01); *A61F 2002/30507* (2013.01); *A61F 2002/30578* (2013.01); *A61F 2002/30604* (2013.01); *A61F 2002/30787* (2013.01); *A61F 2210/0014* (2013.01); *A61F 2210/0066* (2013.01); *A61F 2220/0025* (2013.01); *A61F 2220/0033* (2013.01); *A61F 2230/0065* (2013.01); *A61F 2310/00023* (2013.01); *A61F 2310/00323* (2013.01); *A61F 2310/00359* (2013.01)

(56) References Cited

U.S. PATENT DOCUMENTS

| | | |
|---|---|---|
| 4,135,506 A | 1/1979 | Ulrich |
| 4,501,269 A | 2/1985 | Bagby |
| 4,503,848 A | 3/1985 | Caspar et al. |
| 4,512,038 A | 4/1985 | Alexander et al. |
| 4,599,086 A | 7/1986 | Doty |
| 4,627,853 A | 12/1986 | Campbell et al. |
| 4,678,470 A | 7/1987 | Nashef et al. |
| 4,717,115 A | 1/1988 | Schmitz |
| 4,858,603 A | 8/1989 | Clemow et al. |
| 4,904,261 A | 2/1990 | Dove et al. |
| 4,936,851 A | 6/1990 | Fox et al. |
| 4,950,296 A | 8/1990 | McIntyre |
| 4,955,908 A | 9/1990 | Frey et al. |
| 4,961,740 A | 10/1990 | Ray et al. |
| 4,978,350 A | 12/1990 | Wagenknecht |
| 4,994,084 A | 2/1991 | Brennan |
| 5,026,373 A | 6/1991 | Ray et al. |
| 5,053,049 A | 10/1991 | Campbell |
| 5,062,850 A | 11/1991 | MacMillan et al. |
| 5,071,437 A | 12/1991 | Steffee |
| 5,084,051 A | 1/1992 | Tormala et al. |
| 5,085,660 A | 2/1992 | Lin |
| 5,108,438 A | 4/1992 | Stone et al. |
| 5,112,354 A | 5/1992 | Sires |
| 5,139,424 A | 8/1992 | Yli-Urpo |
| 5,147,404 A | 9/1992 | Downey |
| 5,180,381 A | 1/1993 | Aust et al. |
| 5,192,327 A | 3/1993 | Brantigan |
| 5,211,664 A | 5/1993 | Tepic et al. |
| 5,235,034 A | 8/1993 | Bobsein et al. |
| 5,275,601 A | 1/1994 | Gogolewski et al. |
| 5,281,226 A | 1/1994 | Davydov et al. |
| 5,284,655 A | 2/1994 | Bogdansky et al. |
| 5,290,312 A | 3/1994 | Kojimoto et al. |
| 5,298,254 A | 3/1994 | Prewett et al. |
| 5,314,476 A | 5/1994 | Prewett et al. |
| 5,314,477 A | 5/1994 | Marnay |
| 5,348,788 A | 9/1994 | White |
| 5,397,364 A | 3/1995 | Kozak et al. |
| 5,405,391 A | 4/1995 | Hednerson et al. |
| 5,423,817 A | 6/1995 | Lin |
| 5,439,684 A | 8/1995 | Prewett et al. |
| 5,458,638 A | 10/1995 | Kuslich et al. |
| 5,458,641 A | 10/1995 | Ramirez |
| 5,458,643 A | 10/1995 | Oka et al. |
| 5,489,308 A | 2/1996 | Kuslich et al. |
| 5,507,818 A | 4/1996 | McLaughlin |
| 5,514,180 A | 5/1996 | Heggeness et al. |
| 5,520,690 A | 5/1996 | Errico et al. |
| 5,522,899 A | 6/1996 | Michelson |
| 5,531,746 A | 7/1996 | Errico et al. |
| 5,534,030 A | 7/1996 | Navarro et al. |
| 5,534,031 A | 7/1996 | Matsuzaki et al. |
| 5,549,612 A | 8/1996 | Yapp et al. |
| 5,549,679 A | 8/1996 | Kuslich |
| 5,554,191 A | 9/1996 | Lahille et al. |
| 5,556,430 A | 9/1996 | Gendler |
| 5,569,308 A | 10/1996 | Sottosanti |
| 5,571,190 A | 11/1996 | Ulrich et al. |
| 5,571,192 A | 11/1996 | Schönhöffer |
| 5,593,409 A | 1/1997 | Michelson |
| 5,601,553 A | 2/1997 | Trebing et al. |
| 5,607,474 A | 3/1997 | Athanasiou et al. |
| 5,609,635 A | 3/1997 | Michelson |
| 5,609,636 A | 3/1997 | Kohrs et al. |
| 5,609,637 A | 3/1997 | Biedermann et al. |
| 5,616,144 A | 4/1997 | Yapp et al. |
| 5,676,699 A | 10/1997 | Gogolewski |
| 5,683,394 A | 11/1997 | Rinner |
| 5,683,463 A | 11/1997 | Godefroy et al. |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,713,899 A | 2/1998 | Marnay et al. |
| 5,728,159 A | 3/1998 | Stroever et al. |
| 5,735,905 A | 4/1998 | Parr |
| 5,755,796 A | 5/1998 | Ibo et al. |
| 5,766,253 A | 6/1998 | Brosnahan, III |
| 5,776,194 A | 7/1998 | Mikol et al. |
| 5,776,196 A | 7/1998 | Matsuzaki et al. |
| 5,776,197 A | 7/1998 | Rabbe et al. |
| 5,776,198 A | 7/1998 | Rabbe et al. |
| 5,776,199 A | 7/1998 | Michelson |
| 5,782,915 A | 7/1998 | Stone |
| 5,785,710 A | 7/1998 | Michelson |
| 5,800,433 A | 9/1998 | Benzel et al. |
| 5,861,041 A | 1/1999 | Tienboon |
| 5,865,845 A | 2/1999 | Thalgott |
| 5,865,849 A | 2/1999 | Stone |
| 5,876,402 A | 3/1999 | Errico et al. |
| 5,876,452 A | 3/1999 | Athanasiou et al. |
| 5,885,299 A | 3/1999 | Winslow et al. |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,338 A | 5/1999 | Stone |
| 5,904,719 A | 5/1999 | Errico et al. |
| 5,910,315 A | 6/1999 | Stevenson et al. |
| 5,922,027 A | 7/1999 | Stone |
| 5,944,755 A | 8/1999 | Stone |
| 5,954,722 A | 9/1999 | Bono |
| 5,958,314 A | 9/1999 | Draenert |
| 5,968,098 A | 10/1999 | Winslow |
| 5,972,368 A | 10/1999 | McKay |
| 5,976,187 A | 11/1999 | Richelsoph |
| 5,980,522 A | 11/1999 | Koros et al. |
| 5,981,828 A | 11/1999 | Nelson et al. |
| 5,984,967 A | 11/1999 | Zdeblick et al. |
| 5,989,289 A | 11/1999 | Coates et al. |
| 6,013,853 A | 1/2000 | Athanasiou et al. |
| 6,025,538 A | 2/2000 | Yaccarino, III |
| 6,033,405 A | 3/2000 | Winslow et al. |
| 6,033,438 A | 3/2000 | Bianchi et al. |
| 6,039,762 A | 3/2000 | McKay |
| 6,045,579 A | 4/2000 | Hochshuler et al. |
| 6,045,580 A | 4/2000 | Scarborough et al. |
| 6,056,749 A | 5/2000 | Kuslich |
| 6,066,175 A | 5/2000 | Henderson et al. |
| 6,080,158 A | 6/2000 | Lin |
| 6,080,193 A | 6/2000 | Hochshuler et al. |
| 6,090,998 A | 7/2000 | Grooms et al. |
| 6,096,080 A | 8/2000 | Nicholson et al. |
| 6,096,081 A | 8/2000 | Grivas et al. |
| 6,099,531 A | 8/2000 | Bonutti |
| 6,110,482 A | 8/2000 | Khouri et al. |
| 6,113,638 A | 9/2000 | Williams et al. |
| 6,120,503 A | 9/2000 | Michelson |
| 6,123,731 A | 9/2000 | Boyce et al. |

(56) References Cited

U.S. PATENT DOCUMENTS

| | | |
|---|---|---|
| 6,129,763 A | 10/2000 | Chauvin et al. |
| 6,136,001 A | 10/2000 | Michelson |
| 6,139,550 A | 10/2000 | Michelson |
| 6,143,030 A | 11/2000 | Schroder |
| 6,143,033 A | 11/2000 | Paul et al. |
| 6,156,070 A | 12/2000 | Incavo et al. |
| 6,193,721 B1 | 2/2001 | Michelson |
| 6,193,756 B1 | 2/2001 | Studer et al. |
| 6,200,347 B1 | 3/2001 | Anderson et al. |
| 6,206,922 B1 | 3/2001 | Zdeblick et al. |
| 6,224,602 B1 | 5/2001 | Hayes |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,769 B1 | 6/2001 | Nicholson et al. |
| 6,245,108 B1 | 6/2001 | Biscup |
| 6,258,089 B1 | 7/2001 | Campbell et al. |
| 6,258,125 B1 | 7/2001 | Paul et al. |
| 6,261,291 B1 | 7/2001 | Talaber et al. |
| 6,261,586 B1 | 7/2001 | McKay |
| 6,264,695 B1 | 7/2001 | Stoy |
| 6,270,528 B1 | 8/2001 | McKay |
| 6,306,139 B1 | 10/2001 | Fuentes |
| 6,322,562 B1 | 11/2001 | Wolter |
| 6,342,074 B1 | 1/2002 | Simpson |
| 6,364,880 B1 | 4/2002 | Michelson |
| 6,371,986 B1 | 4/2002 | Bagby |
| 6,371,988 B1 | 4/2002 | Pafford et al. |
| 6,371,989 B1 | 4/2002 | Chauvin et al. |
| 6,375,681 B1 | 4/2002 | Truscott |
| 6,383,186 B1 | 5/2002 | Michelson |
| 6,387,130 B1 | 5/2002 | Stone et al. |
| 6,413,259 B1 | 7/2002 | Lyons et al. |
| 6,423,063 B1 | 7/2002 | Bonutti |
| 6,432,106 B1 | 8/2002 | Fraser |
| 6,447,512 B1 | 9/2002 | Landry et al. |
| 6,447,546 B1 | 9/2002 | Bramlet et al. |
| 6,454,771 B1 | 9/2002 | Michelson |
| 6,458,158 B1 | 10/2002 | Anderson et al. |
| 6,468,311 B2 | 10/2002 | Boyd et al. |
| 6,471,724 B2 | 10/2002 | Zdeblick et al. |
| 6,503,250 B2 | 1/2003 | Paul |
| 6,524,312 B2 | 2/2003 | Landry et al. |
| 6,558,387 B2 | 5/2003 | Errico et al. |
| 6,558,423 B1 | 5/2003 | Michelson |
| 6,562,073 B2 | 5/2003 | Foley |
| 6,569,201 B2 | 5/2003 | Moumene et al. |
| 6,575,975 B2 | 6/2003 | Brace et al. |
| 6,576,017 B2 | 6/2003 | Foley et al. |
| 6,592,624 B1 | 7/2003 | Fraser et al. |
| 6,602,291 B1 | 8/2003 | Ray et al. |
| 6,605,090 B1 | 8/2003 | Trieu et al. |
| 6,616,671 B2 | 9/2003 | Landry et al. |
| 6,620,163 B1 | 9/2003 | Michelson |
| 6,623,486 B1 | 9/2003 | Weaver et al. |
| 6,629,998 B1 | 10/2003 | Lin |
| 6,638,310 B2 | 10/2003 | Lin et al. |
| 6,645,212 B2 | 11/2003 | Goldhahn et al. |
| 6,656,181 B2 | 12/2003 | Dixon et al. |
| 6,679,887 B2 | 1/2004 | Nicholson et al. |
| 6,682,561 B2 | 1/2004 | Songer et al. |
| 6,682,563 B2 | 1/2004 | Scharf |
| 6,695,846 B2 | 2/2004 | Richelsoph et al. |
| 6,695,851 B2 | 2/2004 | Zdeblick et al. |
| 6,709,456 B2 | 3/2004 | Langberg et al. |
| 6,712,818 B1 | 3/2004 | Michelson |
| 6,730,127 B2 | 5/2004 | Michelson |
| 6,736,850 B2 | 5/2004 | Davis |
| 6,761,739 B2 | 7/2004 | Shepard |
| 6,770,096 B2 | 8/2004 | Bolger et al. |
| 6,786,909 B1 | 9/2004 | Dransfeld |
| 6,805,714 B2 | 10/2004 | Sutcliffe |
| 6,808,537 B2 | 10/2004 | Michelson |
| 6,824,564 B2 | 11/2004 | Crozet |
| 6,837,905 B1 | 1/2005 | Lieberman |
| 6,849,093 B2 | 2/2005 | Michelson |
| 6,855,168 B2 | 2/2005 | Crozet |
| 6,863,673 B2 | 3/2005 | Gerbec et al. |
| 6,884,242 B2 | 4/2005 | LeHuec et al. |
| 6,890,334 B2 | 5/2005 | Brace et al. |
| 6,899,735 B2 | 5/2005 | Coates et al. |
| 6,916,320 B2 | 7/2005 | Michelson |
| 6,923,756 B2 | 8/2005 | Sudakov et al. |
| 6,962,606 B2 | 11/2005 | Michelson |
| 6,972,019 B2 | 12/2005 | Michelson |
| 6,972,035 B2 | 12/2005 | Michelson |
| 6,974,479 B2 | 12/2005 | Trieu |
| 6,984,234 B2 | 1/2006 | Bray |
| 7,001,385 B2 | 2/2006 | Bonutti |
| 7,001,432 B2 | 2/2006 | Keller et al. |
| 7,033,394 B2 | 4/2006 | Michelson |
| 7,041,135 B2 | 5/2006 | Michelson |
| 7,044,968 B1 | 5/2006 | Yaccarino et al. |
| 7,060,097 B2 | 6/2006 | Fraser et al. |
| 7,077,864 B2 | 7/2006 | Byrd, III et al. |
| 7,112,222 B2 | 9/2006 | Fraser et al. |
| 7,112,223 B2 | 9/2006 | Davis |
| 7,135,024 B2 | 11/2006 | Cook et al. |
| 7,135,043 B2 | 11/2006 | Nakahara et al. |
| 7,137,984 B2 | 11/2006 | Michelson |
| 7,147,665 B1 | 12/2006 | Bryan et al. |
| 7,163,561 B2 | 1/2007 | Michelson |
| 7,172,627 B2 | 2/2007 | Fiere et al. |
| 7,232,463 B2 | 6/2007 | Falahee |
| 7,232,464 B2 | 6/2007 | Mathieu et al. |
| 7,255,698 B2 | 8/2007 | Michelson |
| 7,276,082 B2 | 10/2007 | Zdeblick et al. |
| 7,320,708 B1 | 1/2008 | Bernstein |
| 7,323,011 B2 | 1/2008 | Shepard et al. |
| 7,534,265 B1 | 5/2009 | Boyd et al. |
| 7,594,932 B2 | 9/2009 | Aferzon et al. |
| 7,608,107 B2 | 10/2009 | Michelson |
| 7,618,456 B2 | 11/2009 | Mathieu et al. |
| 7,637,951 B2 | 12/2009 | Michelson |
| 7,655,042 B2 | 2/2010 | Foley et al. |
| 7,846,207 B2 | 12/2010 | Lechmann et al. |
| 7,862,616 B2 | 1/2011 | Lechmann et al. |
| 7,875,076 B2 | 1/2011 | Mathieu et al. |
| 8,273,127 B2 * | 9/2012 | Jones et al. ............... 623/17.16 |
| 8,328,872 B2 | 12/2012 | Duffield et al. |
| 8,343,222 B2 | 1/2013 | Cope |
| 8,353,913 B2 * | 1/2013 | Moskowitz et al. ......... 606/86 A |
| 8,540,774 B2 | 9/2013 | Kueenzi et al. |
| 2001/0001129 A1 | 5/2001 | McKay et al. |
| 2001/0005796 A1 | 6/2001 | Zdeblick et al. |
| 2001/0010021 A1 | 7/2001 | Boyd et al. |
| 2001/0016777 A1 | 8/2001 | Biscup |
| 2001/0020186 A1 | 9/2001 | Boyce et al. |
| 2001/0031254 A1 | 10/2001 | Bianchi et al. |
| 2001/0039456 A1 | 11/2001 | Boyer, II et al. |
| 2001/0041941 A1 | 11/2001 | Boyer, II et al. |
| 2002/0004683 A1 | 1/2002 | Michelson et al. |
| 2002/0010511 A1 | 1/2002 | Michelson |
| 2002/0016595 A1 | 2/2002 | Michelson |
| 2002/0022843 A1 | 2/2002 | Michelson |
| 2002/0029084 A1 | 3/2002 | Paul et al. |
| 2002/0065517 A1 | 5/2002 | Paul |
| 2002/0082597 A1 | 6/2002 | Fraser |
| 2002/0082603 A1 | 6/2002 | Dixon et al. |
| 2002/0091447 A1 | 7/2002 | Shimp et al. |
| 2002/0095155 A1 | 7/2002 | Michelson |
| 2002/0099376 A1 | 7/2002 | Michelson |
| 2002/0106393 A1 | 8/2002 | Bianchi et al. |
| 2002/0111680 A1 | 8/2002 | Michelson |
| 2002/0128712 A1 | 9/2002 | Michelson |
| 2002/0128717 A1 | 9/2002 | Alfaro et al. |
| 2002/0147450 A1 | 10/2002 | LeHuec et al. |
| 2002/0169508 A1 | 11/2002 | Songer et al. |
| 2002/0193880 A1 | 12/2002 | Fraser |
| 2003/0045939 A1 | 3/2003 | Casutt |
| 2003/0078668 A1 | 4/2003 | Michelson |
| 2003/0125739 A1 | 7/2003 | Bagga et al. |
| 2003/0135277 A1 | 7/2003 | Bryan et al. |

(56) References Cited

U.S. PATENT DOCUMENTS

| | | |
|---|---|---|
| 2003/0153975 A1 | 8/2003 | Byrd |
| 2003/0167092 A1 | 9/2003 | Foley |
| 2003/0195626 A1 | 10/2003 | Huppert |
| 2003/0195632 A1 | 10/2003 | Foley et al. |
| 2003/0199983 A1 | 10/2003 | Michelson |
| 2004/0078078 A1 | 4/2004 | Shepard |
| 2004/0078081 A1 | 4/2004 | Ferree |
| 2004/0093084 A1 | 5/2004 | Michelson |
| 2004/0102848 A1 | 5/2004 | Michelson |
| 2004/0126407 A1 | 7/2004 | Falahee |
| 2004/0176853 A1 | 9/2004 | Sennett et al. |
| 2004/0199254 A1 | 10/2004 | Louis et al. |
| 2004/0210219 A1 | 10/2004 | Bray |
| 2004/0210310 A1 | 10/2004 | Trieu |
| 2004/0210314 A1 | 10/2004 | Michelson |
| 2004/0249377 A1 | 12/2004 | Kaes et al. |
| 2004/0254644 A1 | 12/2004 | Taylor |
| 2005/0015149 A1 | 1/2005 | Michelson |
| 2005/0021143 A1 | 1/2005 | Keller |
| 2005/0033433 A1 | 2/2005 | Michelson |
| 2005/0049593 A1 | 3/2005 | Duong et al. |
| 2005/0049595 A1 | 3/2005 | Suh et al. |
| 2005/0065608 A1 | 3/2005 | Michelson |
| 2005/0071008 A1 | 3/2005 | Kirschman |
| 2005/0085913 A1 | 4/2005 | Fraser et al. |
| 2005/0101960 A1 | 5/2005 | Fiere et al. |
| 2005/0149193 A1 | 7/2005 | Zucherman et al. |
| 2005/0159813 A1 | 7/2005 | Molz |
| 2005/0159818 A1 | 7/2005 | Blain |
| 2005/0159819 A1 | 7/2005 | McCormack et al. |
| 2005/0171606 A1 | 8/2005 | Michelson |
| 2005/0171607 A1 | 8/2005 | Michelson |
| 2005/0177236 A1 | 8/2005 | Mathieu et al. |
| 2005/0240271 A1 | 10/2005 | Zubok et al. |
| 2005/0261767 A1 | 11/2005 | Anderson et al. |
| 2006/0030851 A1 | 2/2006 | Bray et al. |
| 2006/0079901 A1 | 4/2006 | Ryan et al. |
| 2006/0079961 A1 | 4/2006 | Michelson |
| 2006/0085071 A1 * | 4/2006 | Lechmann et al. ........ 623/17.11 |
| 2006/0089717 A1 | 4/2006 | Krishna |
| 2006/0129240 A1 | 6/2006 | Lessar et al. |
| 2006/0136063 A1 | 6/2006 | Zeegers |
| 2006/0142765 A9 | 6/2006 | Dixon et al. |
| 2006/0195189 A1 | 8/2006 | Link et al. |
| 2006/0206208 A1 | 9/2006 | Michelson |
| 2006/0229725 A1 | 10/2006 | Lechmann et al. |
| 2007/0088441 A1 | 4/2007 | Duggal et al. |
| 2007/0118125 A1 | 5/2007 | Orbay et al. |
| 2007/0123987 A1 | 5/2007 | Bernstein |
| 2007/0162130 A1 | 7/2007 | Rashbaum et al. |
| 2007/0168032 A1 | 7/2007 | Muhanna et al. |
| 2007/0219635 A1 | 9/2007 | Mathieu et al. |
| 2007/0225806 A1 | 9/2007 | Squires et al. |
| 2007/0225812 A1 | 9/2007 | Gill |
| 2007/0270961 A1 | 11/2007 | Ferguson |
| 2008/0051890 A1 | 2/2008 | Waugh et al. |
| 2008/0119933 A1 | 5/2008 | Aebi et al. |
| 2008/0133013 A1 | 6/2008 | Duggal et al. |
| 2008/0161925 A1 | 7/2008 | Brittan et al. |
| 2008/0177307 A1 | 7/2008 | Moskowitz et al. |
| 2008/0249569 A1 | 10/2008 | Waugh et al. |
| 2008/0249575 A1 | 10/2008 | Waugh et al. |
| 2008/0269806 A1 | 10/2008 | Zhang et al. |
| 2008/0306596 A1 | 12/2008 | Jones et al. |
| 2009/0076608 A1 | 3/2009 | Gordon et al. |
| 2009/0105830 A1 | 4/2009 | Jones et al. |
| 2009/0210064 A1 | 8/2009 | Lechmann et al. |
| 2010/0016901 A1 | 1/2010 | Robinson |
| 2011/0118843 A1 | 5/2011 | Mathieu et al. |
| 2012/0101581 A1 | 4/2012 | Mathieu et al. |
| 2012/0109309 A1 | 5/2012 | Mathieu et al. |
| 2012/0109311 A1 | 5/2012 | Mathieu et al. |
| 2012/0109312 A1 | 5/2012 | Mathieu et al. |
| 2012/0109313 A1 | 5/2012 | Mathieu et al. |

FOREIGN PATENT DOCUMENTS

| | | | |
|---|---|---|---|
| DE | 3933459 | 4/1991 | |
| DE | 4242889 | 6/1994 | |
| DE | 4409392 | 9/1995 | |
| DE | 4423257 | 1/1996 | |
| DE | 19504867 | 2/1996 | |
| DE | 29913200 | 9/1999 | |
| EP | 0179695 | 4/1986 | |
| EP | 0505634 | 9/1992 | |
| EP | 0517030 | 12/1992 | |
| EP | 0577178 | 1/1994 | |
| EP | 0639351 A2 | 2/1995 | |
| EP | 0517030 B1 | 9/1996 | |
| EP | 0966930 | 12/1999 | |
| EP | 0968692 A1 | 1/2000 | |
| EP | 0974319 | 1/2000 | |
| EP | 0974319 A2 | 1/2000 | |
| EP | 1103236 | 5/2001 | |
| EP | 1033941 | 8/2004 | |
| EP | 0906065 B1 | 9/2004 | |
| EP | 1051133 | 10/2004 | |
| FR | 2552659 | 4/1985 | |
| FR | 2697996 | 5/1994 | |
| FR | 2700947 | 8/1994 | |
| FR | 2727003 | 5/1996 | |
| FR | 2747034 A1 | 10/1997 | |
| FR | 2753368 | 3/1998 | |
| GB | 2148122 A | 5/1985 | |
| GB | 2207607 | 2/1989 | |
| SU | 1465040 A1 | 3/1989 | |
| WO | WO 88/03417 | 5/1988 | |
| WO | WO 88/10100 | 12/1988 | |
| WO | WO 92/01428 | 2/1992 | |
| WO | WO 95/21053 | 8/1995 | |
| WO | WO 96/39988 | 12/1996 | |
| WO | WO 97/20526 | 6/1997 | |
| WO | WO 97/23175 | 7/1997 | |
| WO | WO 97/25941 | 7/1997 | |
| WO | WO 97/25945 | 7/1997 | |
| WO | WO 97/39693 | 10/1997 | |
| WO | WO 98/17209 | 4/1998 | |
| WO | WO 98/55052 | 12/1998 | |
| WO | WO 98/56319 | 12/1998 | |
| WO | WO 98/56433 | 12/1998 | |
| WO | WO 99/27864 | 6/1999 | |
| WO | WO 99/29271 | 6/1999 | |
| WO | WO 99/32055 | 7/1999 | |
| WO | WO 99/38461 | 8/1999 | |
| WO | WO 99/38463 | 8/1999 | |
| WO | WO 99/56675 | 11/1999 | |
| WO | WO 99/63914 | 12/1999 | |
| WO | WO 00/07527 | 2/2000 | |
| WO | WO 00/07528 | 2/2000 | |
| WO | WO 00/25706 | 5/2000 | |
| WO | WO 00/30568 | 6/2000 | |
| WO | WO 00/40177 | 7/2000 | |
| WO | WO 00/41654 | 7/2000 | |
| WO | WO 00/59412 | 10/2000 | |
| WO | WO 00/66044 A1 | 11/2000 | |
| WO | WO 00/66045 | 11/2000 | |
| WO | WO 00/74607 A1 | 12/2000 | |
| WO | WO 01/08611 | 2/2001 | |
| WO | WO 01/56497 | 8/2001 | |
| WO | WO 01/56497 A2 | 8/2001 | |
| WO | WO 01/62190 | 8/2001 | |
| WO | WO 01/80785 | 11/2001 | |
| WO | WO 01/93742 A2 | 12/2001 | |
| WO | WO 01/95837 A1 | 12/2001 | |
| WO | WO 2004/069106 | 8/2004 | |
| WO | WO 2005/007040 A | 1/2005 | |
| WO | WO 2007/098288 | 2/2007 | ................ A61F 2/44 |
| WO | WO 2009/064644 | 5/2009 | |

OTHER PUBLICATIONS

Synthes Zero-P Instruments and Implants Technique Guide dated 2008.

Bray Brochure: InterPlate Vertebral Body Replacement.

(56) References Cited

OTHER PUBLICATIONS

Bray Interplate Spine Fusion Device: Subsidence Control without Stress Shielding.
International Search Report, mailed Mar. 20, 2009, for PCT International Application No. PCT/US08/82473, filed Nov. 5, 2008.
Written Opinion, mailed Mar. 20, 2009, for PCT International Application No. PCT/US08/82473, filed Nov. 5, 2008.
U.S. Appl. No. 61/988,661, filed Nov. 16, 2007, Kueenzi et al.
Chadwick et al., "Radiolucent Structural Materials for Medical Applications," www.mddionline.com/print/238, Jun. 1, 2001, accessed date Jul. 31, 2012, 9 pages.
Jonbergen et al., "Anterior Cervical Interbody fusion with a titanium box cage: Early radiological assessment of fusion and subsidence", The Spine Journal 5, Jul. 2005, 645-649.
Marcolongo et al., "Trends in Materials for Spine Surgery", Comprehensive Biomaterials, Biomaterials and Clinical Use, 6.610, Oct. 2011, 21 pages.
Pavlov et al., "Anterior Lumbar Interbody Fusion with Threaded Fusion Cages and Autologous Grafts", Eur. Spine J., Jun. 2000, 9, 224-229.
Schleicher et al., "Biomechanical Comparison of Two Different Concepts for Stand-alone anterior lumbar interbody fusion", Eur. Spine J., Sep. 2008, 17, 1757-1765.
Scholz et al., "A New Stand-Alone Cervical Anterior Interbody Fusion Device", Spine, Jan. 2009, 34(2), 6 pages.
Spruit et al., "The in Vitro Stabilizing Effect of Polyether-etherketone Cages Versus a Titanium Cage of similar design for anterior lumbar interbody fusion", Eur. Spine J., Aug. 2005, 14 752-758.
International Patent Application No. PCT/CH2003/00089, International Search Report dated Dec. 2, 2003, 3 pgs.
International Search Report, completed Aug. 16, 2007 for International Application No. PCT/US2007/005098, filed Feb. 27, 2007.
U.S. Appl. No. 11/199,599: Amendment/Request for Reconsideration after Non-Final Rejection, dated Sep. 29, 2009, 30 pages.
U.S. Appl. No. 11/199,599: Appeal Brief, dated Apr. 15, 2010, 51 pages.
U.S. Appl. No. 11/199,599: Final Rejection, dated Dec. 24, 2009, 21 pages.
U.S. Appl. No. 11/199,599: Interview Summary included Draft Amendments, dated Sep. 24, 2009, 16 pages.
U.S. Appl. No. 11/199,599: Non-Final Rejection, dated Apr. 1, 2009, 20 pages.
U.S. Appl. No. 11/199,599: Preliminary Amendment, dated Jan. 9, 2008, 11 pages.

\* cited by examiner

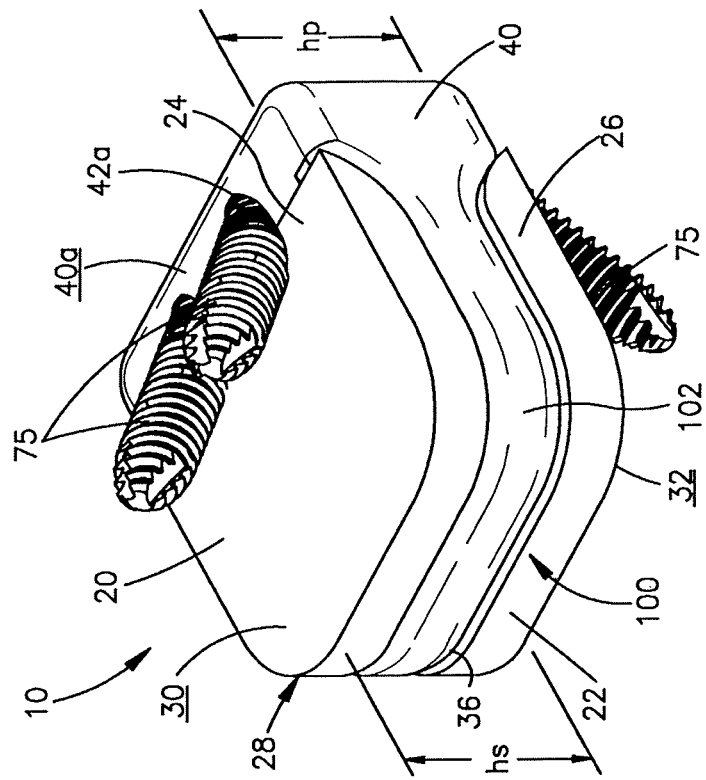
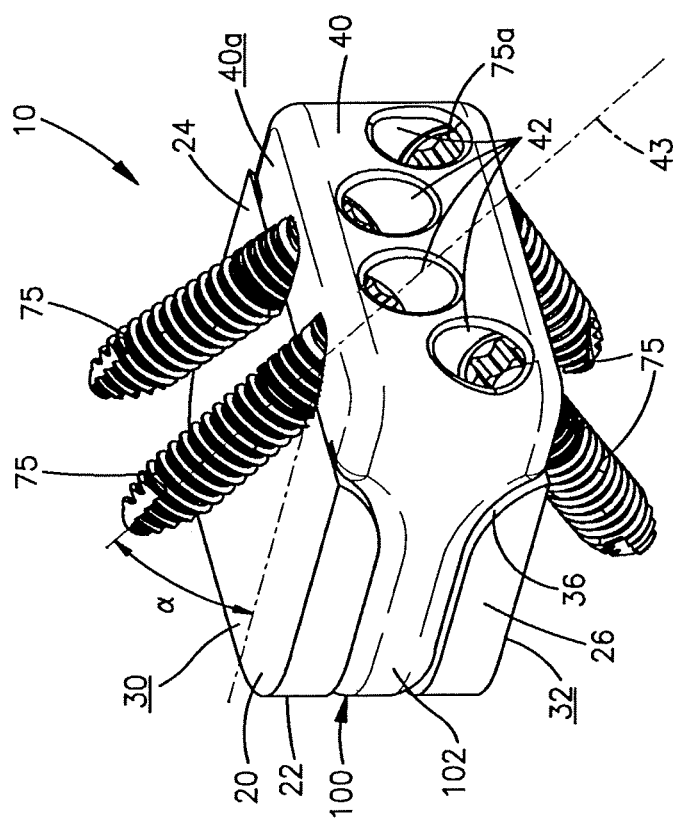

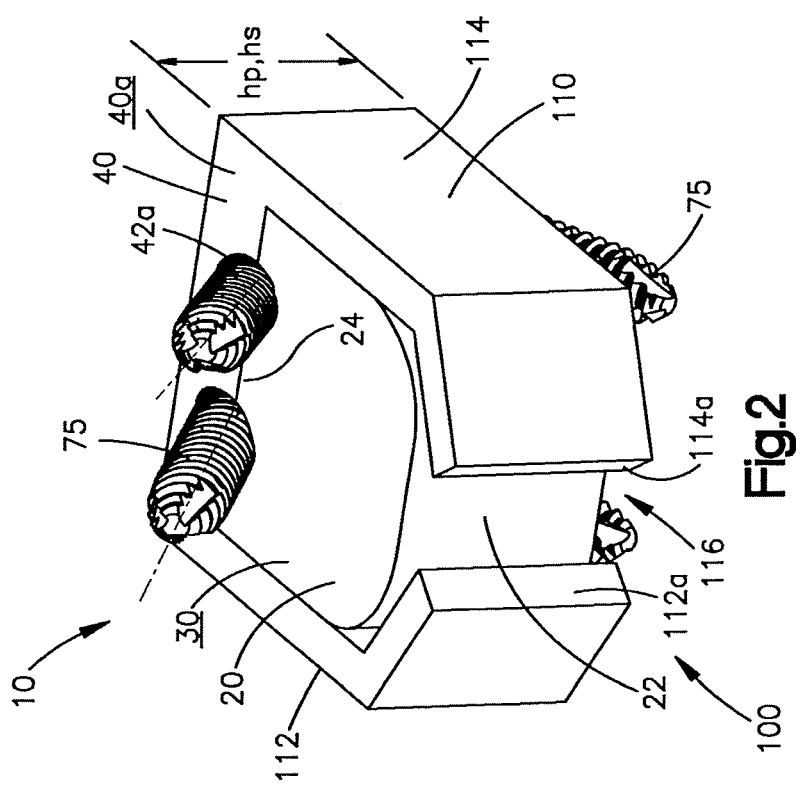

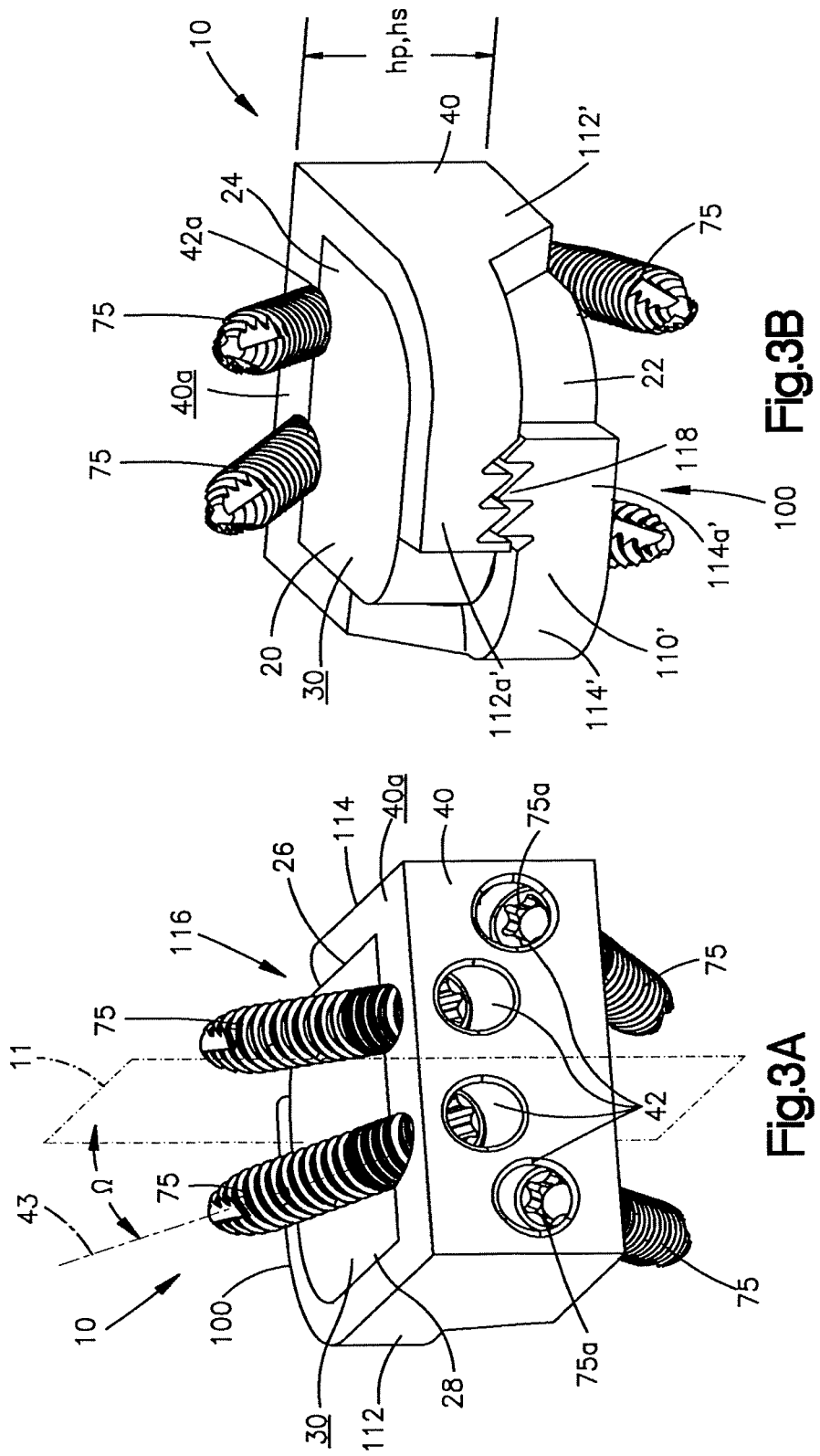

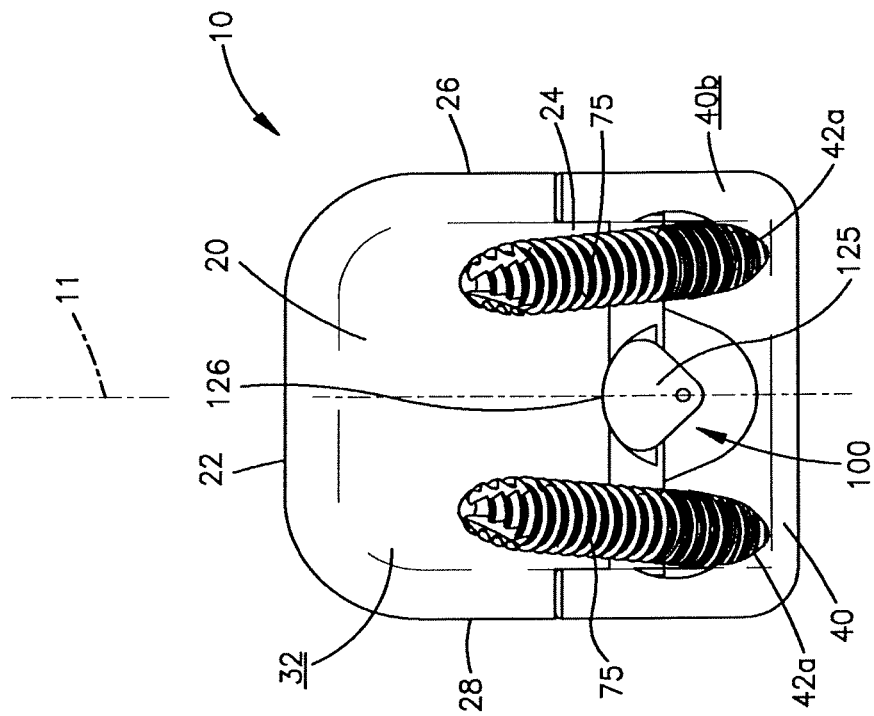
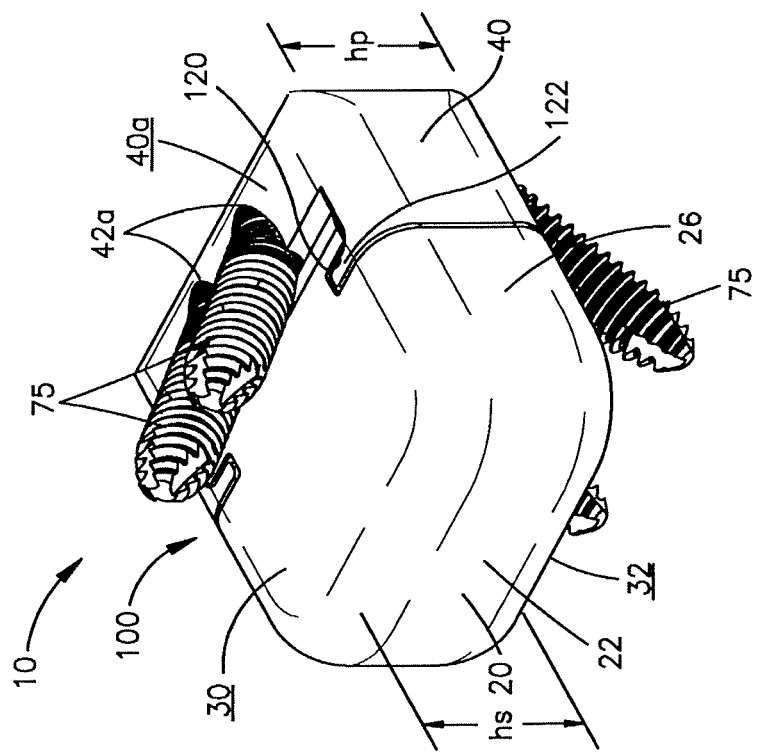

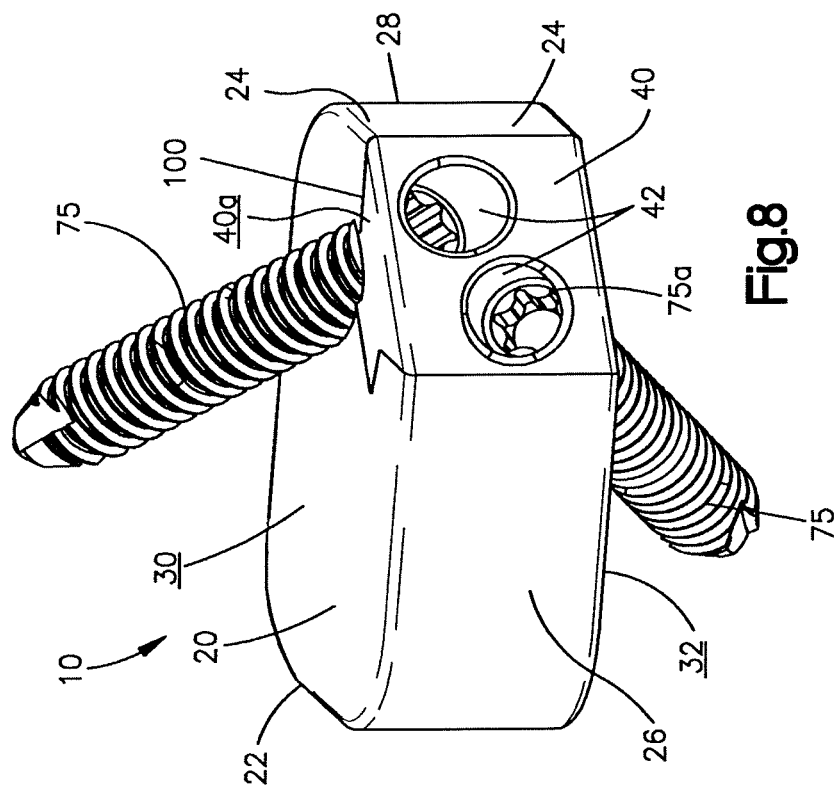
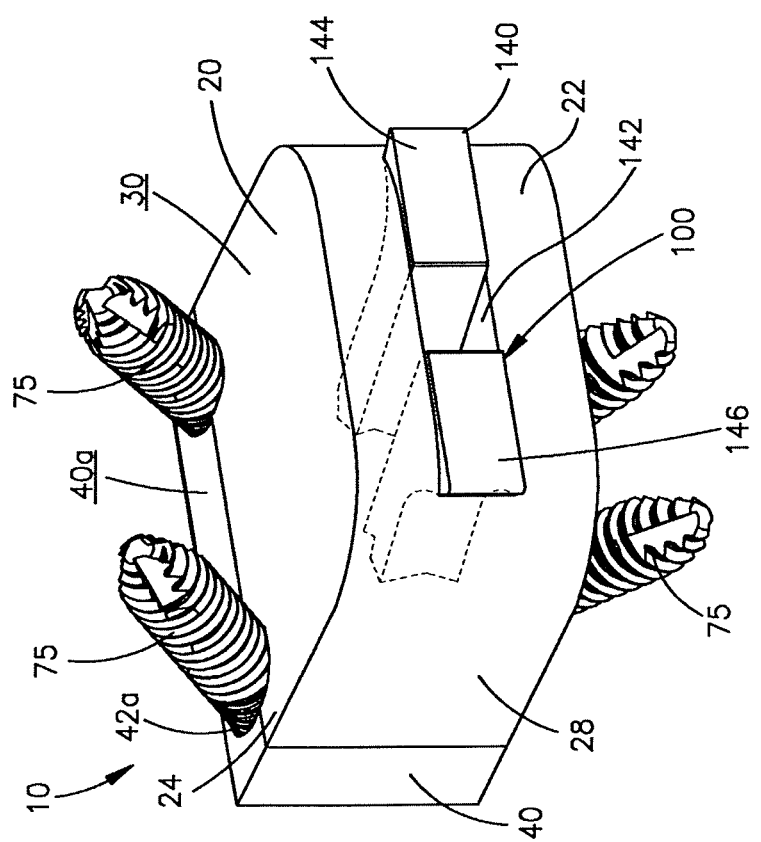

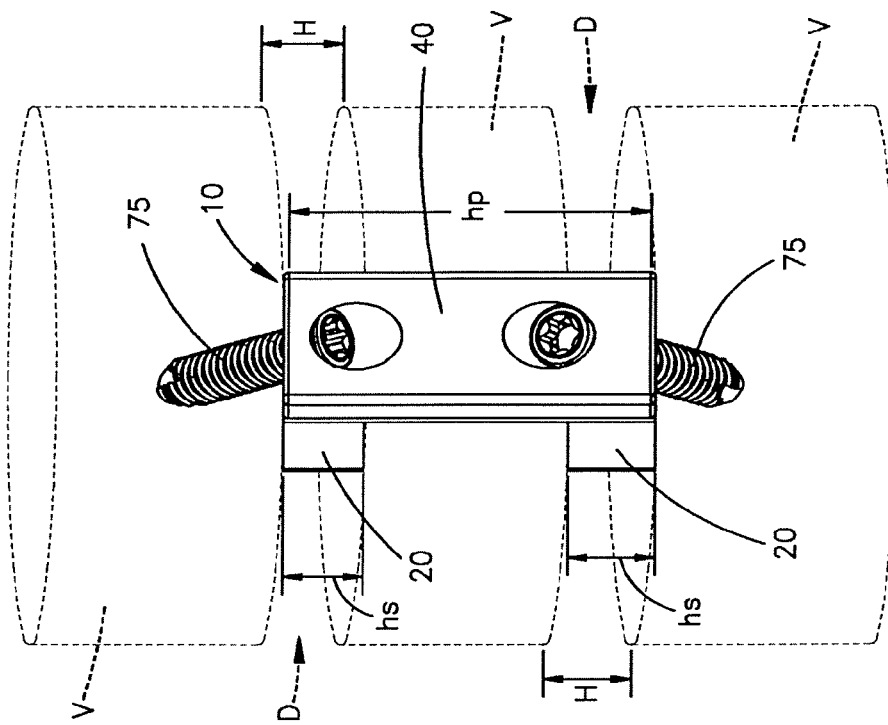
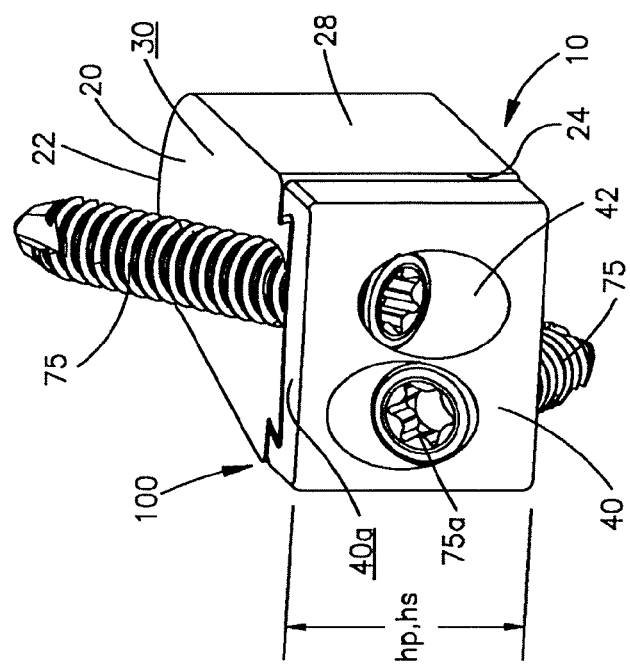

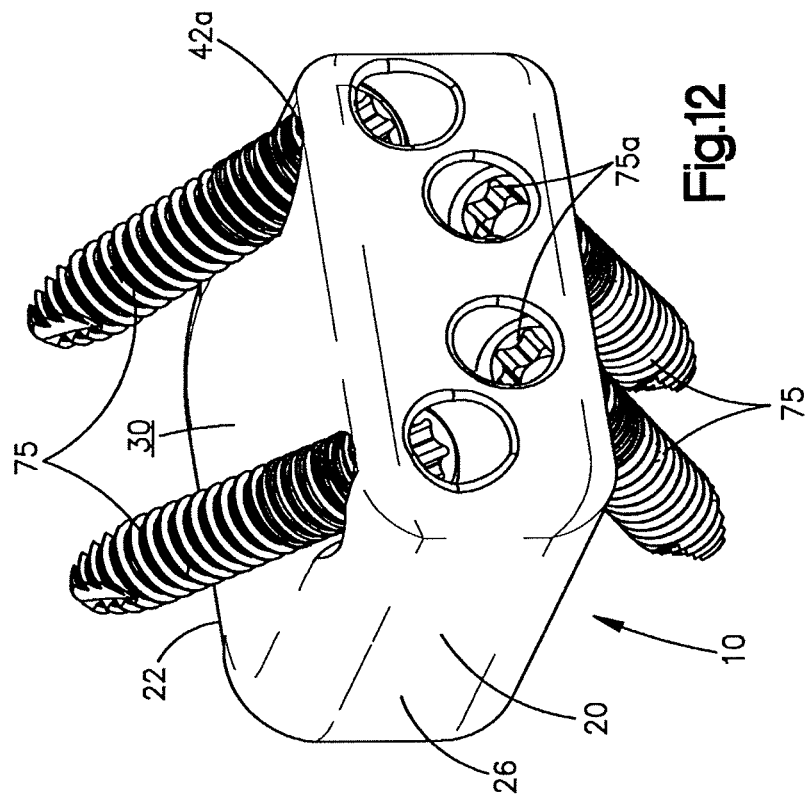
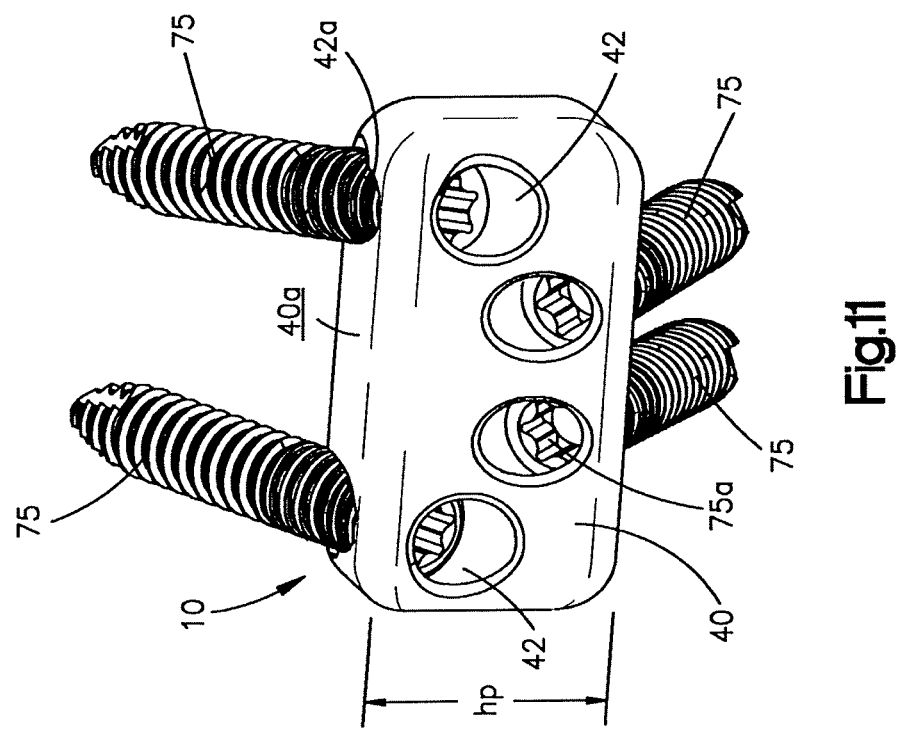

LOW PROFILE INTERVERTEBRAL IMPLANT

CROSS REFERENCE TO RELATED APPLICATIONS

This application is a continuation of U.S. patent application Ser. No. 12/743,098 filed Aug. 25, 2010, which is a U.S. National Phase of International Application No. PCT/US08/82473, filed Nov. 5, 2008, which claims priority to U.S. Provisional Patent Application Ser. No. 60/988,661, filed Nov. 16, 2007, where all of the contents are hereby incorporated by reference in their entireties for all purposes.

FIELD OF THE INVENTION

The present invention relates to an intervertebral implant. More specifically, the preferred embodiment of the present invention relates to a low profile fusion intervertebral implant for implantation into the intervertebral disc space between adjacent vertebral bodies.

BACKGROUND OF THE INVENTION

Millions of people suffer from back pain. In some instances, in order to relieve back pain and/or to stabilize the spinal structure, it becomes necessary to fuse adjacent vertebral bodies at one or more levels. One known method for fusing adjacent vertebral bodies is to implant one or more intervertebral implants into the affected disc space.

SUMMARY OF THE INVENTION

A preferred embodiment of the present invention is directed to a low profile intervertebral implant for implantation in an intervertebral disc space between adjacent vertebral bodies. The intervertebral implant includes a plate preferably coupled to a spacer. The plate is preferably sized and configured so that the plate does not extend beyond the perimeter of the spacer. In this manner, the plate preferably does not increase the height profile of the spacer and the plate may be implanted within the intervertebral disc space in conjunction with the spacer.

In another aspect of the preferred embodiment of the intervertebral implant, the plate is coupled to the spacer by one or more arms extending from the plate. The arms are sized and configured to substantially surround and receive the spacer so that the spacer is securely coupled to the plate. The one or more arms may be a circumferential arm that extends from the plate and which completely wraps around the spacer. The circumferential arm may be sized and configured to shrink as a result of temperature variation. Alternatively, the arms may be a plurality of deformable arms sized and configured to receive the spacer. The arms are preferably deformable to substantially surround and compress against the spacer to secure the spacer to the arms. Alternatively, the one or more arms may be selectively interconnected with one another so that the first and second arms may be placed around the spacer and then tightened to operatively couple the spacer to the plate.

BRIEF DESCRIPTION OF THE DRAWINGS

The foregoing summary, as well as the following detailed description of the preferred embodiments of the application, will be better understood when read in conjunction with the appended drawings. For the purposes of illustrating the preferred intervertebral implants of the present application, there is shown in the drawings preferred embodiments. It should be understood, however, that the application is not limited to the precise arrangements and instrumentalities shown. In the drawings:

FIG. 1A illustrates a rear perspective view of an intervertebral implant in accordance with a first preferred embodiment of the present invention;

FIG. 1B illustrates a top perspective view of the intervertebral implant shown in FIG. 1A;

FIG. 2 illustrates a front perspective view of an intervertebral implant in accordance with a second preferred embodiment of the present invention;

FIG. 3A illustrates a rear perspective view of an intervertebral implant in accordance with a third preferred embodiment of the present invention;

FIG. 3B illustrates a front perspective view of the intervertebral implant shown in FIG. 3A;

FIG. 4A illustrates a top perspective view of an intervertebral implant in accordance with a fourth preferred embodiment of the present invention;

FIG. 4B illustrates a bottom plan view of the intervertebral implant shown in FIG. 4A;

FIG. 7 illustrates a front perspective view of an intervertebral implant in accordance with a seventh preferred embodiment of the present invention;

FIG. 8 illustrates a rear perspective view of an intervertebral implant in accordance with an eighth preferred embodiment of the present invention;

FIG. 9 illustrates a rear perspective view of an intervertebral implant in accordance with an ninth preferred embodiment of the present invention;

FIG. 10 illustrates a rear elevational view of an intervertebral implant in accordance with a tenth preferred embodiment of the present invention, wherein the intervertebral implant is mounted to a spine;

FIG. 11 illustrates a rear perspective view of an intervertebral implant in accordance with an eleventh preferred embodiment of the present invention; and FIG. 12 illustrates a rear perspective view of an intervertebral implant in accordance with a twelfth preferred embodiment of the present invention.

DETAILED DESCRIPTION OF THE INVENTION

Figure 5:
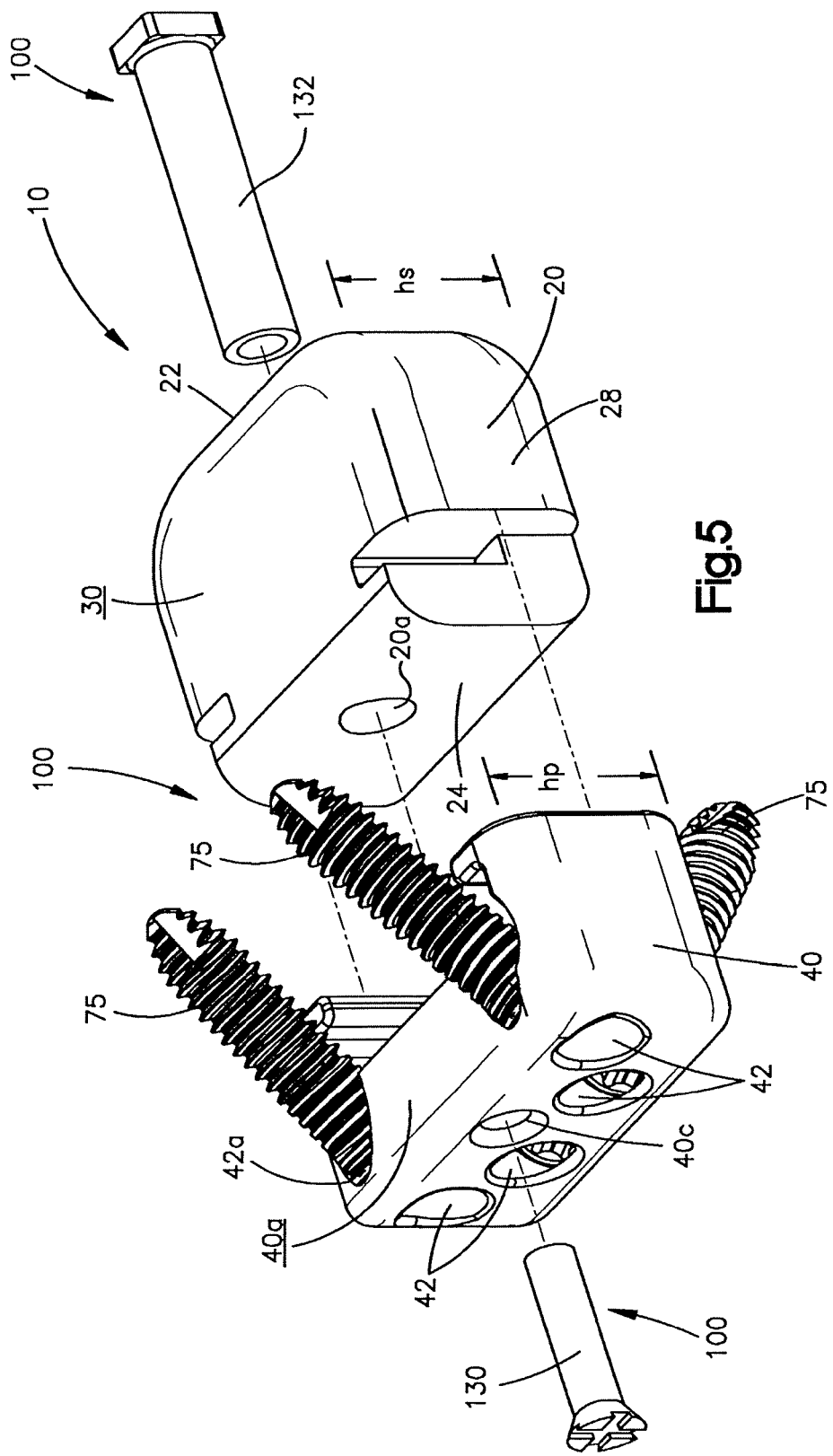
FIG. 5 illustrates a partially exploded top perspective view of an intervertebral implant in accordance with a fifth preferred embodiment of the present invention.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Referring to FIGS. 1A-12, certain exemplary embodiments of the invention will now be described with reference to the drawings. In general, such embodiments relate to a low profile intervertebral implant 10. It should be understood that while the various embodiments of the intervertebral implant 10 will be described in connection with spinal surgery, those skilled in the art will appreciate that the intervertebral implant 10 as well as the components thereof may be used for implantation into other parts of the body. The same reference numerals will be utilized throughout the application to describe similar or the same components of each of the twelve preferred embodiments of the preferred intervertebral implants described herein and the descriptions will focus on the specific features of the individual embodiments that distinguish the particular embodiment from the others.

Generally speaking, the various embodiments of the intervertebral implant 10 are sized and configured to be implanted between adjacent vertebral bodies V. The intervertebral implants 10 may be sized and configured to replace all or substantially all of an intervertebral disc space D between adjacent vertebral bodies V or only part of the intervertebral disc space D. In addition, the preferred intervertebral implants 10 may be configures to replace an entire vertebral body V and related disc spaces D or multiple disc spaces D in a patient's spine, as is apparent to one having ordinary skill in the art.

The intervertebral implants 10 of each of the preferred embodiments preferably include a plate 40 and a spacer 20. The spacer 20 may include a first insertion end portion 22 (e.g., front end), a second end portion 24 (e.g., rear end) opposite the first insertion end portion 22, a first lateral end 26, a second lateral end 28, an upper surface 30, and a lower surface 32. The spacer 20 is preferably configured and dimensioned for implantation into the intervertebral disc space D between adjacent vertebral bodies V. The spacer 20 is preferably sized and configured to maintain and/or restore a desired intervertebral disc height H between the adjacent vertebral bodies V.

The plate 40 is preferably mounted to the second end portion 24 of the spacer 20 and preferably does not extend beyond the perimeter of the spacer 20. That is, a plate height h.sub.p of the plate 40 is preferably no more than a spacer height h.sub.s of the spacer 20 at the second end 24 so that the plate 40 does not increase the height profile of the spacer 20. In this manner, the intervertebral implant 10 has a low profile. Additionally, in this manner, the plate 40 may be entirely implanted into the intervertebral disc space D between the adjacent vertebral bodies V such that the plate 40 does not extend beyond an edge of the disc space D.

The upper and lower surfaces 30, 32 of the spacer 20 may include a series of teeth, one or more keels, or other similar projections (not shown) to aid in securing the intervertebral implant 10 to the endplates of the adjacent vertebral bodies V. Alternatively or in addition, the spacer 20 may include one or more windows or channels (not shown) designed to receive bone graft material. For example, the spacer 20 may include one or more vertical windows or channels (not shown) extending through the spacer 20 from the upper surface 30 to the lower surface 32 for insertion of bone graft material such that bone growth is promoted through the vertical windows or channels following implantation of the intervertebral implant 10. Alternatively or in addition, the spacer 20 may have one or more horizontal windows or channels (not shown) extending through the spacer 20 from the first lateral end 26 to the second lateral end 28 for receiving bone graft material.

The upper and lower surfaces 30, 32 of the spacer 20 may include a curved or a tapered surface to help provide the proper shape to the spine or to orient the endplates of the adjacent vertebral bodies V in a desired manner. The particular surface shape and curvature or taper in the anterior-posterior direction as well as between the first and second lateral ends 26, 28 will depend upon the location the implant 10 is intended to be implanted and/or surgeon preferences.

The intervertebral implant 10 may be constructed of any suitable material or combination of materials including, but not limited to polymer (e.g. PEEK), titanium, titanium alloy, stainless steel, Nitinol, tantalum nitride (TaN), allograft bone, bioresorbable material, magnesium, composites, synthetic bone-welding polymers, etc. The plate 40 may be formed of a different material than the spacer 20. For example, the plate 40 may be formed of a metallic material such as, for example, a titanium or a titanium alloy, and the spacer 20 may be formed of a non-metallic material such as, for example, an allograft, a polymer, a bioresorbable material, a ceramic, etc. Alternatively, the plate 40 and the spacer 20 may be formed from the same material. For example, the plate 40 and the spacer 20 may both be constructed of tantalum nitride (TaN).

The plate 40 preferably includes one or more through holes 42 for receiving fasteners 75 such as, for example, one or more bone screws 75, for securing the intervertebral implant 10 to the adjacent vertebral bodies V. The plate 40 may include any number of through holes 42 arranged in any number of combinations. For example, the plate 40 may include two, three, four or more through holes 42 for receiving, preferably, an equal number of bone screws 75. Moreover, the through holes 42 may alternate with one another with one through hole 42 being angled up and the next through hole 42 being angled down (FIGS. 8 and 9), or the through holes 42 on the outside may be angled up while the through holes 42 on the inside may be angled down (FIGS. 5-7, 11 and 12), etc.

The plate 40 of the preferred embodiments includes at least two through holes 42 configured to receive two fasteners 75 for securing the intervertebral implant 10 to the adjacent vertebral bodies V. The at least two through holes 42 preferably diverge so that at least one fastener 75 is secured into the upper vertebral body V while at least one other fastener 75 is secured into the lower vertebral body V so that opposing forces act on the plate 40 and/or vertebral bodies V. Alternatively, the plate 40 may include three through holes 42 configured to receive three fasteners 75. One fastener 75 may penetrate the upper vertebral body V and two fasteners 75 may penetrate the lower vertebral body V, or vice versa. Alternatively, the plate 40 may include four or more through holes 42 configured to receive four or more fasteners 75. In such a configuration, two inner fasteners 75 may penetrate the upper vertebral body V while two outer fasteners 75 may penetrate the lower vertebral body V, or vice versa, or some combination thereof.

The through holes 42 each include a hole axis 43 such that one of the holes 42 exit through the upper surface of the intervertebral implant 10, possibly through the upper surface 30, for engaging the upper vertebral body V while another of the holes 42 exit through the lower surface of the intervertebral implant 10, possibly through the lower surface 32 for engaging the lower vertebral body V. The fastener 75 that extends through the hole 42, preferably along the hole axis 43 forms a fastener angle a with respect to the upper and lower surfaces 30, 32 of the spacer 20 wherein fastener angle a may be in the range between twenty degrees (20.degree.) and fifty degrees (50.degree.), and most preferably between thirty degrees (30.degree.) and forty-five degrees (45.degree.). The fastener angle .alpha. may be the same for all of the holes 42 or may be different for each of the holes 42.

The though holes 42 formed in the plate 40 preferably are directed outwardly from the center of the intervertebral implant 10, preferably at a lateral fastener angle .OMEGA. Thus, the through holes 42 preferably extend laterally outward from a center plane 11 of the intervertebral implant 10 at the lateral fastener angle .OMEGA. The lateral fastener angle .OMEGA. may be the same for all holes 42 or may be different for each hole 42.

Exit openings 42a of the through holes 42 may be formed in the plate 40 or in the spacer 20. The through holes 42 may also include one or more threads (not shown) for threadably engaging threads formed on a head portion 75a of the bone screw 75 in order to secure the bone screws 75 to the plate 40 and to generally lock the position of the bone screws 75 relative to the plate 40 and/or spacer 20.

The intervertebral implant 10 of the preferred embodiments also preferably includes a coupling mechanism 100 for securing the plate 40 to the spacer 20. Generally speaking, the spacer 20 and the plate 40 are coupled together by the coupling mechanism 100 prior to being implanted into the disc space D. However, in certain embodiments, the intervertebral implant 10 may be configured so that the plate 40 may be coupled to the spacer 20 after one of the spacer 20 and plate 40 have been implanted into the intervertebral disc space. Once coupled, the spacer 20 and plate 40 preferably form a solid implant. The coupling mechanism 100 may be any of the coupling mechanisms 100 described herein or their structural equivalents.

Referring to a first preferred embodiment of the intervertebral implant 10 shown in FIGS. 1A and 1B, the coupling mechanism 100 may be in the form of a solid, circumferential arm 102 that extends from the plate 40. The circumferential arm 102 is preferably sized and configured to wrap around and/or to receive the spacer 20 therein. Preferably, the spacer 20 includes a recess 36 formed on the outer surfaces thereof for receiving at least a portion of the circumferential arm 102.

The circumferential arm 102 may be made from a material that deforms or shrinks as a result of being heated or cooled such as, for example, Nitinol or any other suitable material that deforms as a result of temperature variation. In this manner, the plate 40 may be fixed to the spacer 20 by heating or cooling the plate 40, thereby causing the arm 102 of the plate 40 to shrink, which in turn causes the arm 102 to circumferentially engage the spacer 20. This first preferred embodiment of the is particularly useful since it enables relatively loose tolerances during manufacturing of the spacer 20.

Referring to a second preferred embodiment of the intervertebral implant 10 shown in FIG. 2, the coupling mechanism 100 may be in the form of a split ring 110. That is, the plate 40 may include a pair of arms 112, 114 extending therefrom, wherein the arms 112, 114 are sized and configured to substantially surround the outer circumference of the spacer 20 in order to couple the spacer 20 to the plate 40. The arms 112, 114 are preferably configured so as to be deformable around the spacer 20. That is, the arms 112, 114 are preferably able to deforms so that the arms 112, 114 can wrap around and/or squeeze the spacer 20. The intervertebral implant 10 of the second preferred embodiment is not limited to having the pair of arms 112, 114 and may include nearly any number of arms extending from the plate 40 that are deformable to engage and secure the spacer 20 relative to the plate 40.

As best shown in FIG. 2, the split ring 110 may be include an open gap 116 proximate the first insertion end portion 22 of the implant 10 that defines terminal ends 112a, 114a of the arms 112, 114. The end portions of the arms 112, 114 proximate the terminal ends 112a, 114a are preferably deformable to permit manual clamping of the spacer 20 with the arms 112, 114 to secure the spacer 20 to the plate 40. The gap 116 is not limited to being positioned generally along a midline of the spacer 20 opposite the plate 40 and may be located at nearly any position relative to the plate 40 that permits the arms 112, 114 to deform and clamp or otherwise secure the spacer 20 to the plate 40. For example, the gap 116 may be positioned proximate a corner of the preferred spacer 20 proximate an intersection of the first insertion end portion 22 and one of the first and second lateral ends 26, 28.

Referring to FIGS. 3A and 3B, in a third preferred embodiment of the intervertebral implant 10, the split ring 110' may be sized and configured so that the arms 112', 114' may be interconnected to one another at their terminal ends 112a', 114a' so that, in use, the split ring 110' may be placed around the spacer 20 and then tightened to operatively couple the plate 40 to the spacer 20. The interconnected arms 112', 114' of the split ring 110' of the third preferred embodiment may be tighten by any means including but not limited to a ratcheting locking mechanism 118, a hose clamp design, etc. Incorporation of the split ring 110' of the third preferred embodiment enables the plate 40 to accommodate spacers 20 of variable dimensions and compositions. Furthermore, incorporation of the split ring 110' of the third preferred embodiment may enable the intervertebral implant 10 to be assembled in situ. Other, alternate designs of the plate 40 that allow for the coupling of the plate 40 around the spacer 20 are envisioned. Alternatively, incorporation of the split ring 110' of the third preferred embodiment may enable the surgeon to incorporate bone packing material as opposed to a pre-formed spacer 20 as described herein and as would be apparent to one having ordinary skill in the art.

Referring to the fourth preferred embodiment of the intervertebral implant 10 shown in FIGS. 4A and 4B, the coupling mechanism 100 may be in the form of a recess 120 preferably extending from the upper surface 30 to the lower surface 32 of the spacer 20 to engage a projection 122 formed on and extending from the plate 40 in an assembled configuration. The recess 120 may be formed in the first and second lateral ends 26, 28 of the spacer 20, in only one of the first and second lateral ends 26, 28, centrally within the spacer 20 or otherwise formed for engagement by the projection 122. For example, as shown, the coupling mechanism 100 of the fourth preferred embodiment is in the form of a dovetail joint, wherein the recess 120 is comprised of recesses 120 extending from the top surface 30 toward the bottom surface 32 proximate the second end 24 and the first and second lateral ends 26, 28, respectively. In this fourth preferred embodiment, the coupling mechanism 100 preferably enables the plate 40 to unidirectionally, slidably engage the spacer 20 by sliding the projection 122 into the recess 120, wherein the projection 122 and recess 120 are formed to prevent the spacer 20 from being engaged with the plate 40 unless the spacer 20 is aligned with the plate 40 and slides along a unitary engagement direction. Alternatively, the projection 122 formed on the plate 40 may be sized and configured to flex across the spacer 20 until the projections 122 substantially fit inside the recesses 120 thereby coupling the spacer 20 to the plate 40 via a press-fit arrangement. It should be appreciated that the locations of the projections 122 and the recesses 120 may be reversed so that the spacer 20 includes the projections and the plate 40 includes the recesses, respectively. In addition, the projections 122 and recesses 120 are preferably sized to align the spacer 20 with the plate 40 such that the top surface 30 of the spacer 20 is generally coplanar with a top surface 40a of the plate 40 and a bottom surface 32 of the spacer 20 is generally coplanar or aligned with a bottom surface 40b of the plate 40 in the assembled configuration. Specifically, the projections 122 and the recesses 120 may be tapered to promote the unitary insertion of the spacer 20 into engagement with the plate 40 and alignment of the top and bottom surfaces 40a, 40b of the plate 40 with the top and bottom surfaces 30, 32 of the spacer 20 in the assembled configuration.

In addition, the coupling mechanism 100 of the fourth preferred embodiment may include one or more rotatable cams 125, preferably coupled to the plate 40 to lock the spacer 20 to the plate 40 after the spacer 20 is slid onto the plate 40. Alternatively, the one or more rotatable cams 125 may act as a depth stop to prevent the plate 40 and the spacer 20 from sliding completely past one another as the spacer 20 slides onto the plate 40 to engage the projections 122 with the recesses 120, respectively. The cam 125 may be included on either or both of the upper and lower surfaces of either or both of the plate 40 and spacer 20. Preferably, for example, the plate 40 may include one or more cams 125 on the upper and lower surfaces of the plate 40, wherein the cam 125 is sized and configured to engage one or more recesses 126 formed on the upper and lower surfaces 30, 32 of the spacer 20. In use, the plate 40 and the spacer 20 may be coupled to each other by rotation of the cam 125, which may be accomplished by hand or with the benefit of a tool.

Figure 6:
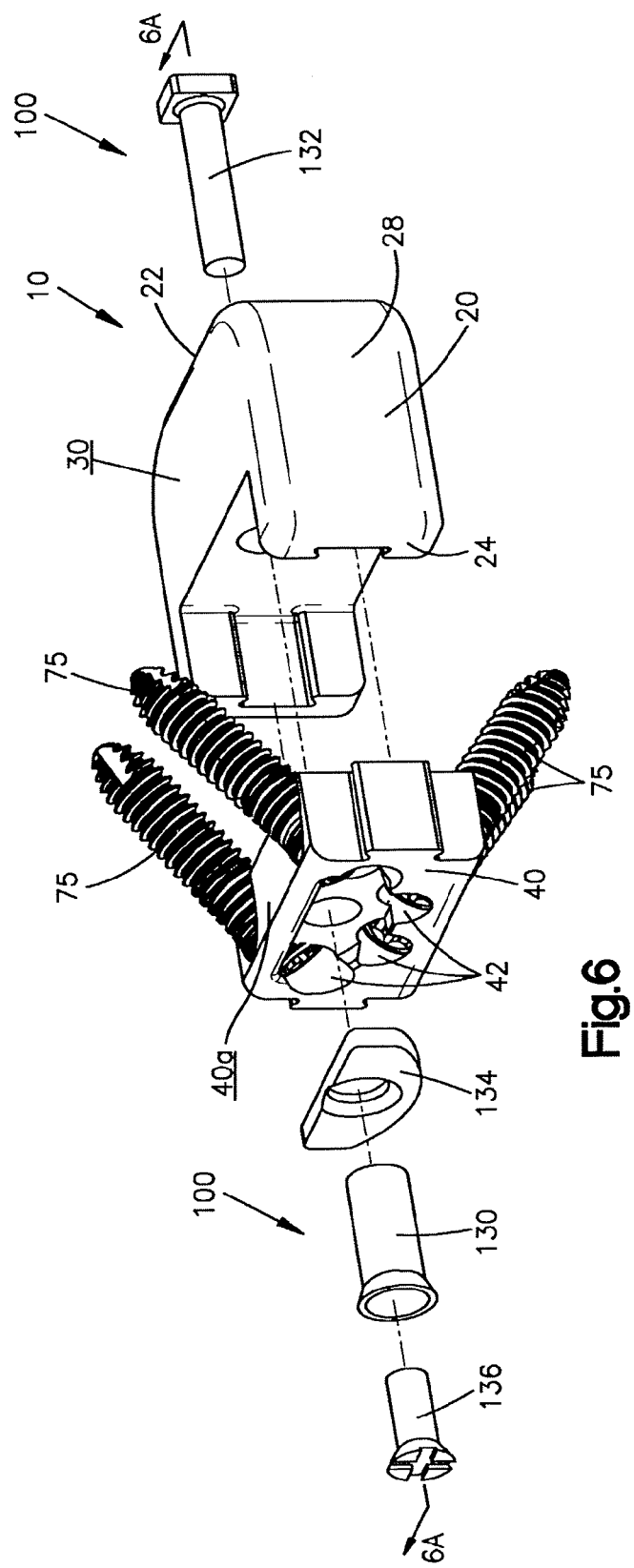
FIG. 6 illustrates a partially exploded side perspective view of an intervertebral implant in accordance with a sixth preferred embodiment of the present invention.
Figure 6A:
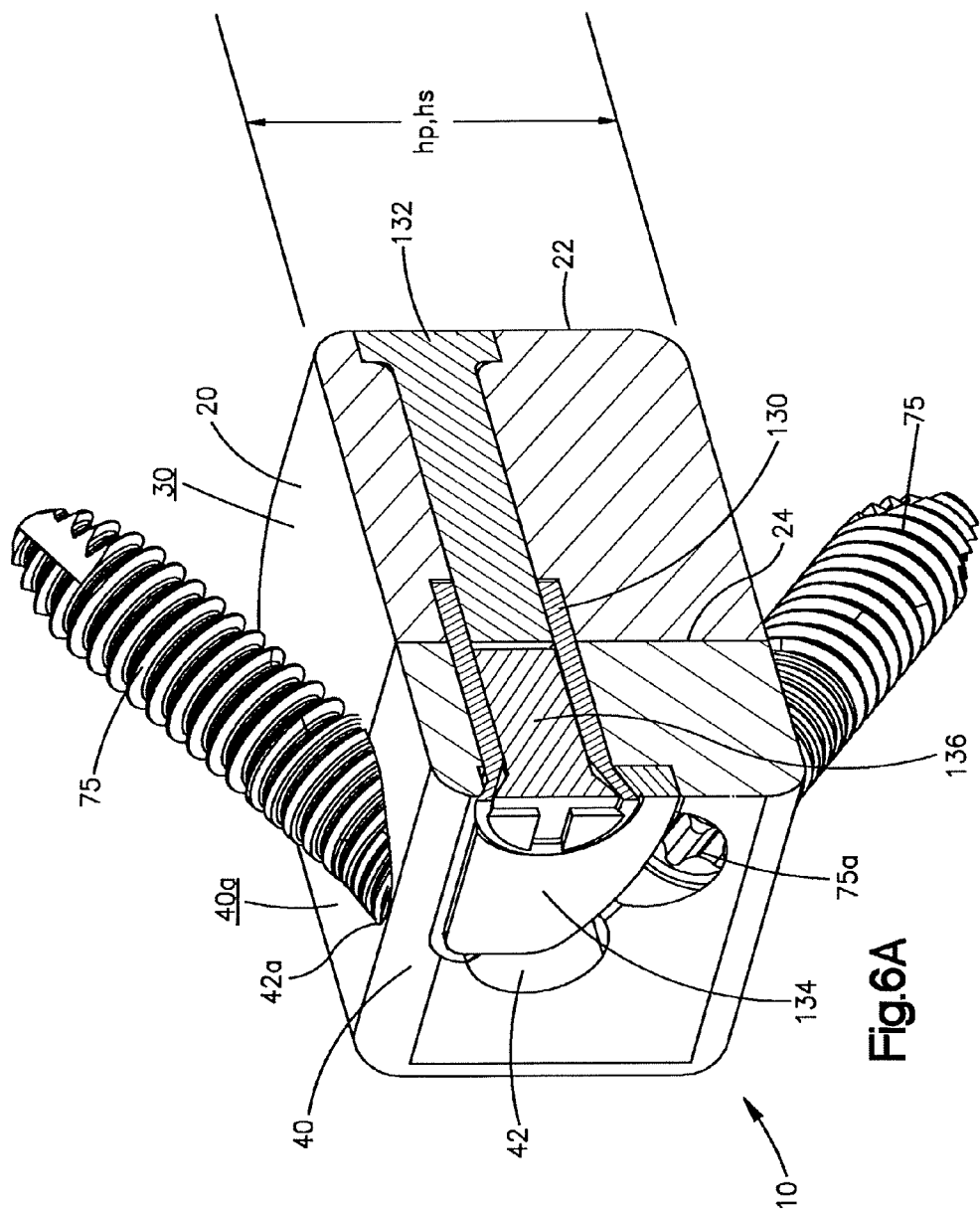
FIG. 6A illustrates a cross-sectional view of the intervertebral implant shown in FIG. 6, taken along line 6a-6a in FIG. 6 with the intervertebral implant in an assembled configuration.

Referring to the fifth preferred embodiment of the intervertebral implant 10 shown in FIG. 5, the coupling mechanism 100 may include a screw 130 that is sized and configured to mate with a nut or barrel threaded pin 132 through first and second holes 20a, 40c in the spacer 20 and the plate 40, respectively. The screw 130 preferably is sized and configured to mate with the nut or barrel threaded pin 132, which may be inserted from the opposite side of the intervertebral implant 10 to secure the spacer 20 to the plate 40. In use, the screw 130 is threadably engaged to the nut or barrel threaded pin 132, thereby coupling the spacer 40 to the plate 20. As best shown in FIGS. 6 and 6A in a sixth preferred embodiment of the intervertebral implant 10, the screw 130' may be cannulated to allow inclusion and use of a blocking plate 134 and a set screw 136 to prevent "backing-out" of the fasteners 75.

Referring to the seventh preferred embodiment of the intervertebral implant 10 shown in FIG. 7, the coupling mechanism 100 may be in the form of a swag plate 140 that extends into and engages the distal end of an aperture 142 formed in the spacer 20. The plate 40 comprises two arms 144, 146 in the preferred embodiment that extend from the plate 40 into the aperture 142. In use, the arms 144, 146 may be urged together at their distal ends and inserted into the aperture 142 until the ends of the arms 144, 146 extend through the aperture 142, at which point, the arms 144, 146 are released so that the ends of the arms 144, 146, preferably protrusions formed thereon, engage the distal end of the aperture 142 of the spacer 20. The arms 144, 146 are able to flex or bend proximate their root or proximal ends such that the distal ends of the arms 144, 146 are able to slide through the aperture 142 during assembly. This embodiment enables the plate 40 to engage the spacer 20 from the inside out. In use, this embodiment enables a relatively simple assembly that permits visualization of the anterior/posterior depth of the implant 10 on an X-ray and assembly of the implant 10 in the operating room.

Referring to the eighth preferred embodiment of the intervertebral implant 10 shown in FIG. 8, the spacer 20 may have a generally rectangular or square-shape with the plate 40 mounted proximate a corner of the spacer 20. The plate 40 may be coupled to the spacer 20 by any coupling mechanisms 100 now or hereafter known for such purpose including those described herein. In use, coupling the plate 40 to a corner of the spacer 20, as opposed to one of the long ends, facilitates implanting of the intervertebral implant 10 into the disc space via an oblique angle. This embodiment is preferably used in cervical applications to limit distract the esophagus, via the approach.

Referring to the ninth preferred embodiment of the intervertebral implant 10 shown in FIG. 9, the intervertebral implant 10 includes a relatively narrow lateral footprint. In use, incorporating a narrower lateral footprint enables the intervertebral implant 10 to accommodate smaller sized patients and/or permits smaller incisions to facilitate minimally invasive techniques. The intervertebral implant 10 of the ninth preferred embodiment may be used as a strut so that the remainder of the area around the implant 10 may be packed with bone chips, putty, bone cement, etc. The intervertebral implant 10 of the ninth preferred embodiment may also enable a transpedicular posterior approach. The intervertebral implant 10 may be used for corpectomy as well as discectomy. It should be noted that any of the embodiments disclosed herein may be sized and configured to include a narrower lateral footprint.

Alternatively and/or in addition, as best shown in FIG. 10, a tenth preferred embodiment of the intervertebral implant 10 includes the plate 40 mounted to two spacers 20 such that the implant 10 is able to span one or more vertebral bodies V.

Referring to the eleventh preferred embodiment of the intervertebral implant 10 shown in FIG. 11, the plate 40 may be implanted between adjacent vertebral bodies without a spacer 20 coupled thereto so that the plate 40 may be implanted between adjacent vertebral bodies to maintain the height of the disc space while leaving the surgeon the option as to whether or not to insert an uncoupled spacer 40, bone chips, bone cement, etc. into the remaining portion of the intervertebral disc space D.

The various coupling mechanisms 100 disclosed herein may also include an adhesive bonding for additional coupling of the plate 40 to the spacer 20. That is, various methods of bonding the spacer 20 to the plate 40 may be used in connection with the various coupling mechanisms 100 disclosed herein. These methods, may include, but are not limited to, chemical bonding or process, ultrasound, ultraviolet light, adhesives, bone welding, clamping etc. These methods may be used in addition, or instead of other coupling mechanisms 100.

Furthermore, referring to a twelfth preferred embodiment of the intervertebral implant 10 shown in FIG. 12, the intervertebral implant 10 may be constructed completely of a monolithic material and has angled bores and fasteners 75. The implant 10 and the fasteners 75 are preferably constructed of the same material, which may be, but is not limited to PEEK, titanium, a resorbable polymer, or magnesium. The implant 10 of the twelfth preferred embodiment may be constructed exclusively of a resorbable material that completely resorbes into a patient's body following implantation. Preferably, the intervertebral implant 10 of the twelfth preferred embodiment is made from an allograft material. The intervertebral implant 10 of the twelfth preferred embodiment may be constructed such that the fasteners 75 are formed from synthetic bone material, which may be inserted and thereafter welded to the adjacent vertebral bodies V to thereby couple the intervertebral implant 10 to the adjacent vertebral bodies V. Alternatively, the synthetic bone material fasteners 75 may be constructed without threads in the form of pins. Such synthetic bone fasteners 75 may be non-threaded or include, for example, push-out resistant Christmas tree threads or other types of threads. Incorporation of synthetic bone material fasteners 75 facilitates manufacturing of the intervertebral implant 10 by eliminating metallic components from the implant 10, thereby enabling constructions using exclusively allograft or resorbable materials.

Alternatively, the intervertebral implant 10 of the twelfth preferred embodiment may incorporate a plate 40 coupled to the spacer 20 and welded to the synthetic bone material fasteners 75 by, for example, ultrasound, thereby eliminating the need for any mechanical locking mechanism when the fasteners are mounted in the through holes 42 in an implanted position. In use, manufacturing the spacer 20 from an allograft or resorbable material and incorporating synthetic bone material fasteners 75 results in only the plate remaining within the patient, if any component of the implant 10 remains within the patient, due to the materials resorbing into the patient's body. It should be noted, however, that it is envisioned that synthetic bone material fasteners 75, which may be welded in-situ to the adjacent vertebral bodies V, may be used in connection with any of the intervertebral implants 10 now or hereafter known including any of the various embodiments of the implant 10 described herein.

The intervertebral implants 10 of each of the twelve preferred embodiments are generally sized and configured for anterior insertion, although different configurations may be possible for lateral, antero-lateral or posterior approaches. In addition to the features described, the intervertebral implant 10 may include threaded holes, slots or channels to mate with instruments to facilitate manipulation and insertion.

Although the present invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art. For example, the present invention may be employed in different sections of the spinal column, including, but not limited to, the cervical area.

The invention claimed is:

1. A low profile intervertebral implant sized and configured to be implanted between adjacent upper and lower vertebral bodies, the implant comprising:

a spacer having a first insertion end, a second end opposite the first insertion end, a first lateral end, a second lateral end opposite the first lateral end, an upper surface that faces the upper vertebral body when the intervertebral implant is implanted between the upper and lower vertebral bodies, a lower surface that faces the lower vertebral body when the intervertebral implant is implanted between the upper and lower vertebral bodies, the first lateral end defines a first recess, and the second lateral end defines a second recess;

a plate configured to be coupled to the spacer by sliding one of the plate and the spacer relative to the other of the plate and the spacer in a direction, the plate comprising a top surface, a bottom surface, a front surface that faces the spacer when the plate is coupled to the spacer, and a rear surface opposite the front surface, wherein the rear surface defines an opening of at least one through hole that is configured to receive a bone screw to secure the implant to one of the adjacent vertebral bodies, the plate further defining a first lateral portion and a second lateral portion that each protrude relative to the front surface of the plate, each of the first and second lateral portions are configured to be inserted into the first and second recesses, respectively, to couple the plate to the spacer; and at least one cam configured to secure the plate to the spacer when the plate is coupled to the spacer, the at least one cam coupled to at least one of the plate and the spacer such that an entirety of the at least one cam is spaced from an entirety of each of the at least one through holes, and the at least one cam is rotatable with respect to the plate from a first position in which the at least one cam prevents the one of the plate and the spacer from sliding completely past the other of the plate and the spacer in the direction, to a second position in which the at least one cam does not prevent the one of the plate and the spacer from sliding completely past the other of the plate and the spacer in the direction.

2. The implant of claim 1, wherein the recesses in the lateral ends of the spacer are formed centrally within the spacer.

3. The implant of claim 1, wherein the protruding first and second lateral portions comprise two or more substantially rectangular projections.

4. The implant of claim 1, wherein the spacer is secured to the plate using one or more screws threaded through one or more holes in the spacer and the plate.

5. The implant of claim 1, wherein a portion of each of the first and second recesses extends from the upper surface to the lower surface of the spacer.

6. The implant of claim 1, wherein the upper surface of the spacer is coplanar with the top surface of the plate and the lower surface of the spacer is coplanar with the bottom surface of the plate.

7. The implant of claim 1, wherein the plate is coupled to the spacer by unidirectionally sliding the protruding first and second lateral portions into the first and second recesses.

8. The implant of claim 1, wherein the plate is configured to be coupled to the spacer by a press-fit arrangement.

9. The implant of claim 1, wherein the first and second recesses and the protruding first and second lateral portions are tapered.

10. The implant of claim 1, wherein the protruding first and second lateral portions are sized and configured to flex across the spacer and to substantially fit inside the first and second recesses, respectively.

11. The implant of claim 1, wherein the upper surface of the spacer comprises a series of teeth.

12. The implant of claim 1, wherein the spacer comprises one or more channels configured to receive bone graft material.

13. The implant of claim 12, wherein the one or more channels extend through the spacer from the upper surface to the lower surface of the spacer.

14. The implant of claim 1, wherein the plate is formed from a first material and the spacer is formed from a second material, the first material being different from the second material.

15. The implant of claim 14, wherein the first material is a metallic material and the second material is non-metallic.

16. The implant of claim 1, wherein the plate has a height $H_p$ measured from the top surface to the bottom surface, the second end of the spacer has a height $H_s$ measured from the upper surface to the lower surface, the height $H_p$ of the plate being equal to or less than the height of the spacer $H_s$ so that the plate does not increase a height profile of the spacer when the plate is coupled to the spacer.

17. The implant of claim 1, wherein the protruding first and second lateral portions extend from the upper surface to the lower surface of the plate.

18. The implant of claim 1, wherein the at least one cam is coupled to either or both of the top surface and the bottom surface of the plate.

19. An intervertebral implant configured to be implanted between an upper vertebral body and a lower vertebral body, the implant comprising:
 a spacer including a first insertion end, a second end opposite the first insertion end, a first lateral end, a second lateral end opposite the first lateral end, an upper surface that faces the upper vertebral body when the intervertebral implant is implanted between the upper and lower vertebral bodies, a lower surface that faces the lower vertebral body when the intervertebral implant is implanted between the upper and lower vertebral bodies, the spacer defining a recess that extends into the first lateral end;
 a plate configured to be coupled to the spacer by sliding one of the plate and the spacer relative to the other of the plate and the spacer in a first direction, the plate including a top surface, a bottom surface, a front surface that faces the spacer in a second direction when the plate is coupled to the spacer, and a rear surface opposite the front surface in a third direction opposite the second direction, the rear surface defining an opening of at least one through hole configured to receive a bone screw, the plate further including a projection spaced from the front surface in the second direction; and a cam configured to secure the plate to the spacer when the plate is coupled to the spacer, the cam configured to be coupled to at least one of the plate and the spacer such that the cam is offset with respect to each of the at least one through holes;
 wherein the projection is configured to be inserted into the recess to couple the plate to the spacer, and when the plate is coupled to the spacer a portion of the spacer is positioned between the front surface and the projection with respect to the second direction.

20. The implant of claim 19, wherein the recess is a first recess, the projection is a first projection, the gap is a first gap, the spacer includes a second recess that extends into the second lateral end, the plate includes a second projection spaced from the front surface in the second direction such that a second gap is defined between the front surface and the second projection.

21. The implant of claim 20, wherein the second projection is configured to be inserted into the second recess to couple the plate to the spacer, and when the plate is coupled to the spacer a portion of the spacer is positioned within the second gap between the front surface and the second projection.

22. The implant of claim 19, wherein the recess extends into the upper surface and terminates within the spacer between the upper surface and the lower surface.

23. The implant of claim 19, wherein the plate has a height $H_p$ measured from the top surface to the bottom surface, the second end of the spacer has a height $H_s$ measured from the upper surface to the lower surface, the height $H_p$ of the plate being equal to or less than the height of the spacer $H_s$ so that the plate does not increase a height profile of the spacer when the plate is coupled to the spacer.

24. The implant of claim 19, wherein the cam is rotatable with respect to the plate from a first position in which the cam prevents the one of the plate and the spacer from sliding completely past the other of the plate and the spacer in the direction, to a second position in which the cam does not prevent the one of the plate and the spacer from sliding completely past the other of the plate and the spacer in the direction.

25. The implant of claim 24, wherein the cam is coupled to either or both of the top surface and the bottom surface of the plate.

26. An intervertebral implant configured to be implanted between an upper vertebral body and a lower vertebral body, the implant comprising:
 a spacer including a first insertion end, a second end opposite the first insertion end, a first lateral end, a second lateral end opposite the first lateral end, an upper surface that faces the upper vertebral body when the intervertebral implant is implanted between the upper and lower vertebral bodies, a lower surface that faces the lower vertebral body when the intervertebral implant is implanted between the upper and lower vertebral bodies, the spacer defining a recess that extends into the first lateral end;
 a plate configured to be coupled to the spacer by sliding one of the plate and the spacer relative to the other of the plate and the spacer in a first direction, the plate including a top surface, a bottom surface, a front surface that faces the spacer in a second direction when the plate is coupled to the spacer, and a rear surface opposite the front surface in a third direction opposite the second direction, the rear surface defining an opening of at least one through hole configured to receive a bone screw, the plate further including a projection spaced from the front surface in the second direction; and a cam configured to secure the plate to the spacer when the plate is coupled to the spacer, such that the cam is rotatable with respect to the plate from a first position in which the cam prevents the one of the plate and the spacer from sliding completely past the other of the plate and the spacer in the direction, to a second position in which the cam does not prevent the one of the plate and the spacer from sliding completely past the other of the plate and the spacer in the direction;
 wherein the projection is configured to be inserted into the recess to couple the plate to the spacer, and when the plate is coupled to the spacer a portion of the spacer is positioned between the front surface and the projection with respect to the second direction.

\* \* \* \* \*